(12) United States Patent
Schultze et al.

(10) Patent No.: US 11,345,129 B2
(45) Date of Patent: May 31, 2022

(54) BARRIER LAMINATES

(71) Applicants: COVESTRO LLC, Pittsburgh, PA (US); COVESTRO DEUTSCHLAND AG, Leverkusen (DE)

(72) Inventors: Dirk Schultze, Florence, MA (US); Lionel Stebbins, Belchertown, MA (US); Andre Kleinheider, Cologne (DE); Helge Kosthorst, Visselhövede (DE)

(73) Assignees: Covestro LLC, Pittsburgh, PA (US); Covestro Deutschland AG, Leverkusen (DE)

( * ) Notice: Subject to any disclaimer, the term of this patent is extended or adjusted under 35 U.S.C. 154(b) by 128 days.

(21) Appl. No.: 16/658,560

(22) Filed: Oct. 21, 2019

(65) Prior Publication Data
US 2021/0113361 A1    Apr. 22, 2021

(51) Int. Cl.
| | |
|---|---|
| *B32B 27/30* | (2006.01) |
| *B32B 7/12* | (2006.01) |
| *B32B 27/08* | (2006.01) |
| *B32B 27/32* | (2006.01) |
| *B32B 27/40* | (2006.01) |

(52) U.S. Cl.
CPC .............. *B32B 27/306* (2013.01); *B32B 7/12* (2013.01); *B32B 27/08* (2013.01); *B32B 27/32* (2013.01); *B32B 27/40* (2013.01); *B32B 2250/24* (2013.01); *B32B 2255/10* (2013.01); *B32B 2255/26* (2013.01); *B32B 2307/7265* (2013.01)

(58) Field of Classification Search
CPC ......... B32B 7/12; B32B 27/306; B32B 27/08; B32B 27/32; B32B 27/40
USPC ........................................................ 428/213
See application file for complete search history.

(56) References Cited

U.S. PATENT DOCUMENTS

| | | | |
|---|---|---|---|
| 5,593,775 A | 1/1997 | Hargarter et al. | |
| 5,866,257 A * | 2/1999 | Schledjewski | B32B 27/18 428/423.1 |
| 6,946,182 B1 | 9/2005 | Allgeuer | |
| 9,144,464 B2 | 9/2015 | Knowlton et al. | |
| 2007/0237916 A1* | 10/2007 | Rasmussen | B32B 25/10 428/35.2 |
| 2013/0025764 A1* | 1/2013 | Henderson | A01N 25/34 156/60 |
| 2021/0113361 A1* | 4/2021 | Schultze | B32B 27/08 |

* cited by examiner

*Primary Examiner* — Betelhem Shewareged
(74) *Attorney, Agent, or Firm* — John E. Mrozinski, Jr.

(57) ABSTRACT

The present invention provides a barrier film comprising a first layer formed from thermoplastic polyurethane (TPU) and a second layer formed from a thermoplastic polymer-based coupling agent containing an ethylene-vinyl acetate (EVA) copolymer and a second polar co-monomer polymer, wherein the barrier film has a total thickness of between 50 μm (2 mil) and 600 μm (24 mil), wherein the first layer has a thickness of between 20 μm (0.8 mil) and 400 μm (16 mil), and wherein the second layer has a thickness of between 20 μm (0.8 mil) and 200 μm (8 mil). The inventive barrier film may find use in colostomy, urostomy, and ileostomy pouches and in other medical applications.

17 Claims, 1 Drawing Sheet

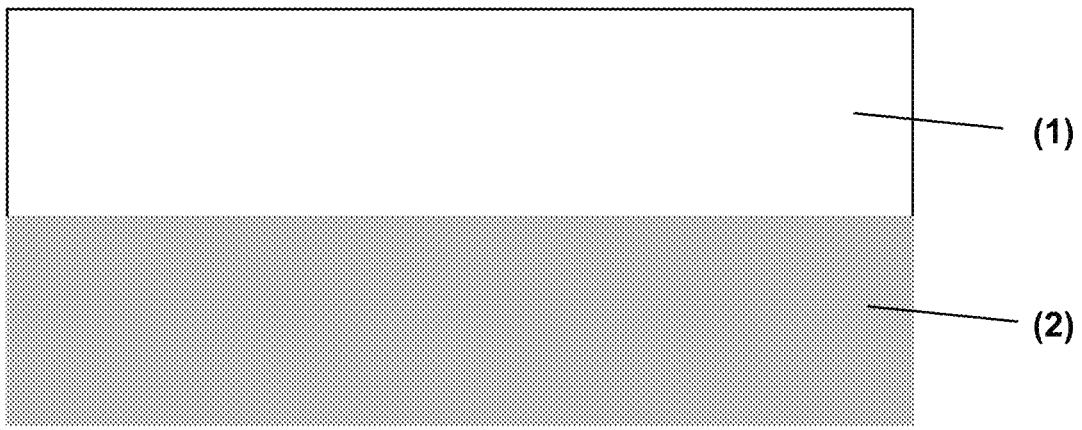

BARRIER LAMINATES

FIELD OF THE INVENTION

The present invention relates in general to films and more specifically to barrier films for use in ostomy pouches and other medical applications.

BACKGROUND OF THE INVENTION

The complex demands of applications in the medical field frequently requires the combination of advantageous properties of a variety of materials. Obstacles may be encountered owing to the limited compatibility of different polymers.

Medical barrier films are often designed to address quality of life aspects of people whose medical history/conditions require the use of ostomy (e.g., colostomy, urostomy, and ileostomy) pouches or other collection pouches.

In such situations, barrier properties are important to keep any unpleasant odors and moisture inside the pouch whilst it is worn. In addition, such films provide excellent performance in terms of seal ability and seal integrity, liquid and gas barrier, mechanical integrity and dimensional stability. Ostomy bags produced from barrier materials typically include polyvinylidene chloride (PVDC) as the barrier material.

Historically, polyethylene has been the outer layer of choice; more recent developments have used ethylene/vinyl acetate copolymers (EVA) to improve the flexibility of the bag itself.

Pouching systems typically consist of a collection pouch plastic bag. Simple ones are one-piece systems whereas more sophisticated two-piece systems involve a mounting plate, commonly called a flange, wafer or a baseplate, and a collection pouch that is attached mechanically or with an adhesive in an airtight seal.

The major requirements for materials to be considered for the construction of ostomy bags are pliability, barrier to odor, low weight and a comfortable feel to the skin. These requirements are typically met in existing laminates by combining a barrier film, which may be a monolayer or multilayer construction, typically in the range of 60 to 100 µm thick, with a skin contact substrate material, e.g. a non-woven which is secured to the barrier film through a peripheral pouch seal.

Medical device materials must also exhibit the appropriate barrier properties necessary to maintain the proper composition of the fluids with which they interact, ensuring that oxygen, moisture and potential contaminants cannot penetrate through films or tubes. These devices must also possess the durability to stand up to the rigors and fast pace of the medical environment, regardless of their rigidity. Finally, medical devices must be made with a material that demonstrates a clear history of biocompatibility.

A need exists in the art for better barrier films that combine the advantageous properties of thermoplastic polyurethane with those of olefinic based materials.

SUMMARY OF THE INVENTION

Accordingly, the present invention provides a barrier film which allows the combination of thermoplastic polyurethane (TPU)-based materials with olefinic materials. To overcome potentially detrimental adhesion deficits between the olefinic outer layer of the barrier film and the polyurethane (PU) layer, a special bridging layer is also provided.

These and other advantages and benefits of the present invention will be apparent from the Detailed Description of the Invention herein below.

BRIEF DESCRIPTION OF THE FIGURES

The present invention will now be described for purposes of illustration and not limitation in conjunction with the FIGURES, wherein:

FIG. 1 shows a cross sectional view of the inventive barrier film.

DETAILED DESCRIPTION OF THE INVENTION

The present invention will now be described for purposes of illustration and not limitation. Except in the operating examples, or where otherwise indicated, all numbers expressing quantities, percentages, and so forth in the specification are to be understood as being modified in all instances by the term "about."

Any numerical range recited in this specification is intended to include all sub-ranges of the same numerical precision subsumed within the recited range. For example, a range of "1.0 to 10.0" is intended to include all sub-ranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited in this specification is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein. All such ranges are intended to be inherently described in this specification such that amending to expressly recite any such sub-ranges would comply with the requirements of 35 U.S.C. § 112(a), and 35 U.S.C. § 132(a). The various embodiments disclosed and described in this specification can comprise, consist of, or consist essentially of the features and characteristics as variously described herein.

Any patent, publication, or other disclosure material identified herein is incorporated by reference into this specification in its entirety unless otherwise indicated, but only to the extent that the incorporated material does not conflict with existing definitions, statements, or other disclosure material expressly set forth in this specification. As such, and to the extent necessary, the express disclosure as set forth in this specification supersedes any conflicting material incorporated by reference herein. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicant reserves the right to amend this specification to expressly recite any subject matter, or portion thereof, incorporated by reference herein.

Reference throughout this specification to "various non-limiting embodiments," "certain embodiments," or the like, means that a particular feature or characteristic may be included in an embodiment. Thus, use of the phrase "in various non-limiting embodiments," "in certain embodiments," or the like, in this specification does not necessarily refer to a common embodiment, and may refer to different embodiments. Further, the particular features or characteristics may be combined in any suitable manner in one or more embodiments. Thus, the particular features or characteristics illustrated or described in connection with various or certain embodiments may be combined, in whole or in part, with the features or characteristics of one or more other embodiments without limitation. Such modifications and variations are intended to be included within the scope of the present specification.

The grammatical articles "a", "an", and "the", as used herein, are intended to include "at least one" or "one or more", unless otherwise indicated, even if "at least one" or "one or more" is expressly used in certain instances. Thus, these articles are used in this specification to refer to one or more than one (i.e., to "at least one") of the grammatical objects of the article. By way of example, and without limitation, "a component" means one or more components, and thus, possibly, more than one component is contemplated and may be employed or used in an implementation of the described embodiments. Further, the use of a singular noun includes the plural, and the use of a plural noun includes the singular, unless the context of the usage requires otherwise.

In a first aspect, the present invention is directed to a barrier film comprising a first layer formed from thermoplastic polyurethane (TPU) and a second layer formed from a heat-activated, olefin-based polymer coupling agent containing at least ethylene-vinyl acetate (EVA) copolymer and a second polar co-monomer, wherein the packaging material has a total thickness of between 2 mil (50 µm) and 24 mil (600 µm), the first layer has a thickness of between 0.8 mil (20 µm) and 16 mil (400 µm), and the second layer has a thickness of between 0.8 mil (20 µm) and 8 mil (200 µm). The inventive barrier film may find use in ostomy (e.g., colostomy, urostomy, and ileostomy) pouches and in other medical applications.

In a second aspect, the present invention is directed to a method of constructing an ostomy pouch, the method comprising joining an olefinic film with a barrier film comprising a first layer formed from thermoplastic polyurethane (TPU) and a second layer formed from a heat-activated, olefin-based polymer coupling agent containing at least ethylene-vinyl acetate (EVA) copolymer and a second polar co-monomer, wherein the packaging material has a total thickness of between 2 mil (50 µm) and 24 mil (600 µm), the first layer has a thickness of between 0.8 mil (20 µm) and 16 mil (400 µm), and the second layer has a thickness of between 0.8 mil (20 µm) and 8 mil (200 µm) to form a multilayer film and forming a pouch comprising a first wall and a second wall joined together to define a closed compartment having an interior from the multilayer film.

Of particular interest in the present invention is the combination of elastomers with barrier materials. A layered film is provided to bridge adhesion properties between polyurethane (PU) and barrier films available in the art.

The inventive barrier film may comprise two or, preferably more layers. Conventional gas and odor barrier materials may be used, such as vinylidene chloride copolymers with a co-monomer, for example an acrylic ester, acrylic acid, and vinyl chloride, or an ethylene-vinyl alcohol copolymer, or vinylidene fluoride-vinyl fluoride copolymer, or polyamides, or mixtures thereof, with the optional addition of chlorinated paraffin, stabilizers and waxes.

Structured approaches may include PVDC (poly-vinylidene chloride) layers embedded between polyolefin layers. Preferred are coextruded films including a PVDC and also an EVA (ethylene-vinyl alcohol) copolymer layer (e.g., PVDC/EVA films), particularly EVA/PVDC/EVA.

Films comprising an EVA (ethylene-vinyl alcohol) copolymer and preferably also comprising an EVA layer are also of interest, preferably an EVA/Tie/EVOH/Tie/EVA barrier material. The "Tie" layer may preferably be selected from modified EVA. films In addition, the use of EVA as an outer layer allowed for sealing procedures like high (radio) frequency welding.

Materials involved with odor proof multilayer constructions are described, for example, in U.S. Pat. No. 5,470,624. Materials suitable for skin contacts are selected to be as discrete as possible, e.g. through their soft touch and low noise or quietness. The highly flexible materials from the polyurethanes group provide these properties. Also, the flexibility of the ostomy bag construction is considered more and more important as adhesives, flanges or highly elastic apertures of pouches are required.

Processing techniques include coating and laminating of adhesives or in the case of flanges welding well away from the aperture of the pouch, so that the aperture is enabled to be stretched and molded to the required shape and size.

Polyurethane materials are known to those in the art for their versatility and suitability to form materials ranging from adhesives, foams to solid elastomers. Adhesives suitable for medical applications can e.g. be formed from polyurethane dispersions. Solid elastomers can e.g. be found in the group of thermoplastic polyurethanes (TPU).

Thermoplastic polyurethanes (TPU) are well known to those in the art for their abrasion stable characteristics and may provide solutions for pouches/bags, nested blister packaging, and composite blister packaging. TPU is a robust material and TPU products demonstrate high tear strength and resistance, durability even for soft grades, good chemical resistance, desired clarity, important abrasion resistance, and outstanding cold temperature performance. Pouches consisting of only TPU would not provide sufficient barrier properties for small gauge films.

Ostomy bags must be durable enough on the outside to resist perforation, but must still exhibit appropriate barrier properties to regulate the transmission of odors. Tensile strength is necessary for burst, tear and cut resistance. Thermoplastic polyurethanes (TPUs) allow for product resilience and are desirable for applications where there is mechanical risk.

Thermoplastic polyurethanes (TPUs) are soft over a wide temperature range without using plasticizers and their base chemistry allows them to be tailored to specific needs. The absence of plasticizer can help reduce the risk of health complications known to be caused by such chemicals.

In particular, thermoplastic polyurethane (TPU) formulations can be created with the usage requirements of the medical industry in mind—there are no plasticizers involved in TPU production, and the material does not exude any harmful by-products. Thermoplastic polyurethanes (TPUs) are known for their reliably in the medical field and selected formulations have long been certified as biocompatible.

Thermoplastic polyurethanes (TPUs) are known to those in the art for their skin friendliness and biocompatibility and thermoplastic processes such as welding and sealing may be used. Ease of sealing is necessary to ensure the longevity of medical products. Techniques such as ultrasound and solvent welding provide a more efficient and consistent weld quality than previously used methods.

Because of the customization properties of thermoplastic polyurethane (TPU), it is an ideal material for use in the construction of various medical devices, such as tubes and fluid storage bags. The safety of TPU products with regard to their use on or within the body is important, as medical products must often transmit drugs, blood or other fluids, and thus materials used in their development must not exude any harmful substances that could leach into these fluids and compromise fluid integrity.

Thermoplastic polyurethanes (TPUs) are also considered to be the material of choice for flanges and apertures of medical devices.

Polyurethane dispersions are the material of choice to form skin-friendly adhesive layers with an adhesive strength that can be adjusted to application requirements. Accordingly, adjusted formulations are established in the medical arts.

The present invention provides a solution in form of a multilayer composite film structure intended for laminating or sealing to barrier materials. Such laminates can subsequently be laminated, welded, or overmolded with thermoplastic polyurethane (TPU) based materials to form flanges or apertures. Alternatively, the film according to the invention can be coated ahead with other polyurethane materials.

As shown in FIG. 1, the composite film according to the invention includes a first layer 1 essentially including thermoplastic polyurethane (TPU) and a second layer 2 containing at least one modified ethylene-vinyl-acetate (EVA) copolymer.

In some embodiments, layer 2 comprises ethylene-vinyl-acetate (EVA) copolymers modified by thermoplastic polyurethane (TPU), by blending both, TPU, and EVA improved bonding to different polymers. This blend approach provides excellent bonding characteristics to TPU and rigid thermoforming polymers. In this embodiment, films according to the invention contain at least one layer of a TPU/EVA blend.

The second layer 2 contains polar co-monomers, such as disclosed in U.S. Pat. No. 5,593,775. Ethylene is preferred as co-monomer. In the packaging material according to the invention, at least two different polar, oxygen-containing olefin copolymers A and B are mixed and melted together under sufficient shear. The total proportion of polar oxygen-containing co-monomer units in various embodiments is between 18 wt. % and 40 wt. %, with reference to the total weight of polymer resin used. The olefin co-monomer A should be present in larger amounts, with a total proportion of at least 60% of the total weight of co-monomer units. In certain embodiments, the co-monomers used for the polar olefin copolymers A and B are methacrylic acid and/or its salts and/or esters and/or acrylic acid and/or its salts and/or its esters and/or vinyl acetate, in the unsaponified and/or saponified form.

Thermoplastic polyurethane (TPU) ether-based films are preferred over TPU ester-based films due to their improved hydrolysis resistance.

To manufacture multilayer structures, the known thermal forming procedures for the processing of plastic materials are suitable. In particular, co-extrusion techniques are suitable and preferred for the better levels of bond strength among the layers. Blown film co-extrusion is a particularly preferred method to produce films according to the invention.

Additionally, the co-extrusion manufacture of a film comprising a plain thermoplastic polyurethane (TPU) layer facing one surface, at least one TPU/EVA layer facing the other surface for bonding purposes improves the performance. The co-extrusion process opens options for further bridging by combining with additional layers.

Thermoplastic polyurethane (TPU) and ethylene-vinyl-acetate (EVA) are accessible to thermoplastic techniques due to a joint processing window. This makes them suitable partners for enhancing adhesion properties. Use of this joint thermoplastic window can be made in the film extrusion process, also allowing for co-extrusion of various layers at temperatures of from 160° C. to 200° C.

During manufacturing, films can be subject to surface treatment, such that at least one of the outer layers has been subject to a chemical or physical treatment.

Adhesive modified ethylene-vinyl-acetate (EVA) provides improved adhesion properties between thermoplastic polyurethane (TPU) and structured olefin surfaces. Adhesion properties can be introduced by either inserting an adhesive layer between TPU and olefin, or blending TPU with olefin. In another embodiment, this may be done by providing a bridging second layer 2 combining the compatibility through blending TPU with EVA and having a TPU surface layer.

Adhesive properties for second layer 2 show a most suitable performance for TPU/EVA blend ratio of between 0.3 and 3.0 mass-%. Preferably, the blend ratio between a TPU and a modified EVA is between 0.7 and 1.5 mass-%.

Additional improvement may be made by selecting maleic acid anhydride (MSA) as a modifying component for ethylene-vinyl-acetate (EVA). EVA MSA ter-polymers can be randomly copolymerized, or more preferably, MSA can be grafted to an EVA backbone providing further improvement. One preferred embodiment is a film consisting of at least two layers: one from TPU providing abrasion stability 1, one from a TPU/EVA blend providing adhesion 2.

In some embodiments, the coupling substance resins being used for the second layer 2, contain ethylene, vinyl acetate, and maleic acid anhydride as co-monomers, with a total amount of maleic acid anhydride for the coupling substance not exceeding 5000 ppm.

First layer 1 of the film according to the invention comprises at least one TPU elastomer, preferably from linear TPU elastomers, of which the longer chain diol component is a polyester of polyether, with a Shore hardness of preferably 75-95 A, measured according to ASTM D 2240.

The film according to the invention can be laminated or welded directly adjacent or well away from the aperture of the pouch enabling the aperture to be stretched and molded to the required shape and size.

In some embodiments, the thermoplastic composite film according to the invention is laminated to the olefinic outer side of a barrier film at larger dimensions than an aperture. Thus, by being stretched and molded to the required size, the risk of failure of the laminate can be avoided.

The film according to the invention may also be coated with, preferably, polyurethane-based adhesives and subsequently sealed to state of the art barrier films.

For the multilayer structure according to the invention, TPU ether-based film layers are preferred over TPU ester-based film layers due to their improved hydrolysis resistance.

Suitable thermoplastic polyurethanes are, for example, available under the trade names DESMOPAN, ELASTOLLAN, ESTANE, MORTHANE, and TEXIN.

Films according to this invention contain within the first (TPU) layer 1 additional processing additives from the group including, but not limited of:

I. anti-blocking agents, inorganic or organic spacers;
II. slip or separation aids, typically surface active;
III. pigments or fillers; and
IV. stabilizers.

The total of additives I to IV in selected embodiments is between 0% and 30%, in certain embodiments, the total is between >0% and 30%.

In various embodiments, films have a total thickness between 2 mil (50 µm) and 24 mil (600 µm). In those embodiments, the layer thickness for the first (TPU) layer 1 is between 0.8 mil (20 µm) and 16 mil (400 µm), and the gauge of the second (blend) layer 2 is between 0.8 mil (20 µm) and 8 mil (200 µm).

Films according to the invention may be useful for bridging otherwise incompatible polymer materials. They can be laminated to flexible plastic materials and they advantageously are accessible by various thermal and solvent based sealing methods.

In addition to ostomy pouches, another application for the inventive films is for combining olefinic barrier films and three dimensional thermoplastic polyurethane (TPU) parts. Preferred are welded flanges and apertures from TPU to extruded flat structures.

EXAMPLES

The non-limiting and non-exhaustive examples that follow are intended to further describe various non-limiting and non-exhaustive embodiments without restricting the scope of the embodiments described in this specification. All quantities given in "parts" and "percents" are understood to be by weight, unless otherwise indicated.

The following examples and comparison examples were manufactured by blown film extrusion. The extrusion process suitable for processing thermoplastic materials has been described among others by Wortberg, Mahlke and Effen in: *Kunststoffe,* 84 (1994) 1131-1138, by Pearson in: *Mechanics of Polymer Processing,* Elsevier Publishers, New York, 1985 or company Davis-Standard in: *Paper, Film & Foil Converter* 64 (1990) pp 84-90. Blown film tools to shape the melt into film shape are explained by Rauwendaal in: *Polymer Extrusion,* Hanser Publishers, New York 1986 or Michaeli in: *Extrusions-Werkzeuge,* Hanser Verlag, Munich 1991.

Example 1

Using a two layer blown film die, a coextruded film was manufactured comprising a first layer formed from a thermoplastic polyurethane (TPU)-ether of a Shore-A-hardness 89, measured according to ASTM D2240, corresponding to a hardness of 36 Shore-D. The TPU-ether had a melt flow index (MFI) of 25 g/10 min @ 190° C./21.6 kg according to ISO 1133-1 and a specific gravity of 1.12 g/cm$^3$ according to ISO 1183-1 and a thermomechanical analysis (TMA) onset temperature of 165° C. This 100 µm layer contained the processing additives 2.5% diatomaceous earth and 0.3% amide wax. All ingredients for this first layer were processed in a single extruder.

The second layer was an ethylene-vinyl-acetate (EVA) copolymer having an MFI of 3.5 g/10 min @ 230° C./2.16 kg according to ISO 1133-1 and a specific gravity of 0.94 g/cm$^3$ according to ISO 1183-1 which was grafted with maleic anhydride. The VA content of the resin was 28 mass-percent and maleic anhydride below 4000 ppm. The Shore hardness was at 80 A/27 D according to ASTM D2240. The TMA onset temperature was 75° C. The second layer had a thickness of 50 µm.

The extrusion tools were set to temperatures between 160° C. and 200° C. The two melt streams were joined in a two layer blown film die at a processing temperature of 195° C. and ejected through a circular die with a diameter of 130 mm. The circular melt was cooled by blowing chilled air against it. The film subsequently collapsed, was laid flat, separated and was wound up.

Example 2

Using a two layer blown film die, a coextruded film was manufactured from a first layer formed from a thermoplastic polyurethane (TPU)-ether of a Shore-A-hardness 89, measured according to ASTM D2240, corresponding to a hardness of 36 Shore-D. The TPU ether had a MFI of 25 g/10 min @ 190° C./21.6 kg according to ISO 1133-1 an d a specific gravity of 1.12 g/cm$^3$ according to ISO 1183-1 and a TMA onset temperature of 165° C. This 90 µm layer contained the processing additives 2.5% diatomaceous earth and 0.3% amide wax. All ingredients for this first layer were processed in a single extruder.

The second layer was a blend of 50% by weight of TPU ether with an MFI of 25 @ 190° C./21.6 kg according to ISO 1133-1 and a specific gravity of 1.12 g/cm$^3$ according to ISO 1183-1 at a Shore A hardness of A 89/D36 according to ASTM D2240 and a TMA onset temperature of 165° C. 50% by weight consisted of a grafted ethylene-vinyl acetate/maleic anhydride copolymer with an MFI of 3.5 g/10 min @ 230° C./2.16 kg according to ISO 1133-1 and a specific gravity of 0.94 g/cm$^3$ according to ISO 1183-1. The VA content of the resin was at 28 mass-percent and maleic anhydride below 4000 ppm. The Shore hardness was at 80 A/27 D according to ASTM D2240. The TMA onset temperature was at 75° C. The second layer had a thickness of 60 µm.

The extrusion tools were set to temperatures between 160° C. and 200° C. The two melt streams were joined in a two layer blown film die at a processing temperature of 195° C. and ejected through a circular die with a diameter of 130 mm. The circular melt was cooled by blowing chilled air against it. The film subsequently collapsed, was laid flat, separated and was wound up.

Comparative Example 1

Using a mono layer blown film die, a film was manufactured consisting of a thermoplastic polyurethane (TPU)-ether of a Shore-A-hardness 89, measured according to ASTM D2240, corresponding to a hardness of 36 Shore-D. The TPU ether had a MFI of 25 g/10 min @ 190° C./21.6 kg according to ISO 1133-1 and a specific gravity of 1.12 g/cm$^3$ according to ISO 1183-1 and a TMA onset temperature of 165° C. This 150 µm layer contained processing additives 2.5% diatomaceous earth and 0.3% amide wax. All ingredients for this layer were processed in a single extruder.

The extruder was operated at temperatures between 160° C. and 200° C. The melt streams was inserted into a blown film die at a processing temperature of 195° C. and ejected through a lip set of 130 mm diameter. The circular melt was cooled by blowing chilled air against it. The film subsequently collapsed, was laid flat, separated and was wound up.

Comparative Example 2

Using a two layer blown film die, a coextruded film was manufactured consisting of a layer formed from a thermoplastic polyurethane (TPU)-ester of a Shore-A-hardness 90, measured according to ASTM D2240, corresponding to a hardness of 40 Shore-D. The TPU ester had a MFI of 60 g/10 min @ 190° C./21.6 kg according to ISO 1133-1 an d a specific gravity of 1.22 g/cm³ according to ISO 1183-1 and a TMA onset temperature of 170° C. This 30 μm layer contained processing additives of 5% diatomaceous earth and 1% amide wax. All ingredients for this layer were processed in a single extruder.

A second layer was made essentially of a linear hydroxyl polyester polyurethane. This flexible hot melt adhesive polyurethane with a high rate of crystallization has typically outstanding adhesion on a large number of materials. Extruded flat products made from this raw material are known to be of high quality. This TPU ester with a viscosity of 1200 m Pas measured according to ISO 3219 and a specific gravity of 1.16 g/cm³ according to ISO 1183-1 at a Shore A hardness of A 94/D 45 according to ASTM D2240 and a TMA onset temperature of 55° C. The second layer h ad a thickness of 20 μm.

The extrusion tools were set to temperatures between 130° C. and 180° C. The melt streams were joined in a multilayer blown film die at a processing temperature of 180° C. and ejected through a set of circular lips with a diameter of 300 mm. The circular melt was cooled by blowing chilled air against it. The film subsequently collapsed, was laid flat, separated and was wound up.

Comparative Example 3

Using a mono layer circular blown film die, a film was manufactured consisting of a 115 μm (4.5 mil) low-density polyethylene (PE). The PE had an MFI of 0.4 g/10 min ISO 1133-1 @ 190° C., 2.16 kg, a density of 0.92 g/cm³ ISO 1183-1, and a hardness of 94 A Shore measured according to ASTM D2240, corresponding to a hardness of 45 Shore-D. The PE had a TMA onset temperature of 103° C.

The extruder was operated at temperatures between 160° C. and 195° C. The melt stream was inserted into a blown film die at a processing temperature of 190° C. and ejected through a lip set of 130 mm diameter. The circular melt was cooled by blowing chilled air against it. The film subsequently collapsed, was laid flat, separated and was wound up.

Evaluation and comparison of the properties of the samples and comparison samples according to the invention considers adhesion to barrier films as important.

Lamination of films made as samples and comparative examples was carried out using a HOTRONIX laminator. The films according to the examples and comparative were laminated against a three layer film EVA/PVDC/EVA of 75 μm (3 mil) thickness. Lamination was carried out at 150° C. for 10 seconds.

The visual descriptions of manual separation, as well as the pull test results from a testing device were determined.

For the Pull Test 1 in./25.4 mm wide sample strips were cut out of the laminates using a parallel blade sample cutter. The separation force was determined using a regular samples clamps and load cell of a tensile testing set up.

To demonstrate the bridging, a molded thermoplastic polyurethane (TPU) part was welded to the laminated film. The welding result and failure mode upon applying force between barrier film and molded part were compared.

In the following Table I, characteristic data of the samples and comparison examples are given.

TABLE I

| Property | Example 1 | Example 2 | Comparative Example 1 | Comparative Example 2 | Comparative Example 3 |
|---|---|---|---|---|---|
| | EVA Layer facing EVA | TPU/EVA blend layer facing EVA | | Hot melt adhesive polyurethane layer facing EVA | |
| Pull Test - Description | Film failure* - Very Good bond | Film failure* - Very Good bond | Bond failure | Bond failure - Very weak bond | Film failure* - Very Good bond |
| Pull Test - Peel Strength g/in. (gf) | 1341 | 1014 | 123 | 4 | 1379 |
| TPU part welding success | Good | Good | Good | Good | None |
| Failure mode of structure | No layer separation, barrier film failure | No layer separation, barrier film failure | Layer separation TPU/ barrier film | Layer separation TPU/ barrier film | Layer separation TPU/ laminate film |

*Failing film: 3 mil 3 layer barrier film EVA/PVDC/EVA

These data show clearly that films according to the invention are superior to comparative films.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth herein. Such embodiments may be obtained, for example, by combining, modifying, or reorganizing any of the disclosed steps, components, elements, features, aspects, characteristics, limitations, and the like, of the various non-limiting embodiments described in this specification. In this manner, Applicant reserves the right to amend the claims during prosecution to add features as variously described in this specification, and such amendments comply with the requirements of 35 U.S.C. § 112(a), and 35 U.S.C. § 132(a).

Various aspects of the subject matter described herein are set out in the following numbered clauses:

Clause 1. A barrier film comprising a first layer formed from thermoplastic polyurethane (TPU) and a second layer formed from a heat-activated, olefin-based polymer coupling agent containing at least ethylene-vinyl acetate (EVA) copolymer and a second polar co-monomer, wherein the barrier film has a total thickness of between 50 μm (2 mil) and 600 μm (24 mil), wherein the first layer has a thickness of between 20 μm (0.8 mil) and 400 μm (16 mil), and wherein the second layer has a thickness of between 20 μm (0.8 mil) and 200 μm (8 mil).

Clause 2. The barrier film according to Clause 1, wherein the ethylene-vinyl acetate (EVA) copolymer contains at least 15% vinyl acetate.

Clause 3. The barrier film according to one of Clauses 1 and 2, wherein the first layer has a Shore hardness, measured according to ASTM D 2240, of 75-95 A Clause 4. The barrier film according to any one of Clauses 1 to 3, wherein the second layer comprises a blend of thermoplastic polyurethane (TPU) and ethylene-vinyl acetate (EVA) copolymer.

Clause 5. The barrier film according to any one of Clauses 1 to 4, wherein the ethylene-vinyl acetate (EVA) copolymer includes maleic anhydride in an amount of less than 5000 ppm.

Clause 6. The barrier film according to any one of Clauses 1 to 5, wherein the second layer comprises a blend of a thermoplastic polyurethane (TPU) and a modified ethylene-vinyl acetate (EVA) at a ratio between 0.3 mass-percent and 3.0 mass-percent Clause 7. The barrier film according to any one of Clauses 1 to 6, wherein the second layer comprises a blend of a thermoplastic polyurethane (TPU) and a modified ethylene-vinyl acetate (EVA) at a ratio between 0.7 mass-percent and 1.5 mass-percent.

Clause 8. The barrier film according to any one of Clauses 1 to 7, wherein the second polar co-monomer is selected from the group consisting of vinyl acetate, acrylic acid, acrylic acid esters, acrylic acid salts, methacrylic acid, methacrylic acid esters, and methacrylic acid salts.

Clause 9. The barrier film according to any one of Clauses 1 to 8, wherein between 0% and 30% of an additive selected from the group consisting of anti-blocking agents, inorganic or organic spacers, slip or separation aids, pigments, fillers, and stabilizers, is added to the first layer.

Clause 10. The barrier film according to any one of Clauses 1 to 9, wherein the film is produced in a co-extrusion process at a temperature of from 160° C. to 200° C.

Clause 11. The barrier film according to any one of Clauses 1 to 9, wherein the film is produced in a blown film co-extrusion process at a temperature of from 160° C. to 200° C.

Clause 12. The barrier film according to any one of Clauses 1 to 11, wherein at least one layer is subjected to a physical or chemical surface treatment.

Clause 13. The barrier film according to any one of Clauses 1 to 12 further comprising an adhesive layer applied to the first layer.

Clause 14. The barrier film according to Clause 13, wherein the adhesive comprises a polyurethane.

Clause 15. A laminated structure comprising the barrier film according to any one of Clauses 1 to 14 joined to an olefin-based film.

Clause 16. The laminated structure according to Clause 15, wherein the olefin is polyethylene.

Clause 17. The laminated structure according to one of Clauses 15 and 16, wherein the barrier film and the olefin-based are joined by a thermal joining method selected from the group consisting of thermo lamination and flame bonding.

Clause 18. An aperture comprising the laminated structure according to any one of Clauses 15 to 17.

Clause 19. An ostomy pouch comprising a barrier film comprising a first layer formed from thermoplastic polyurethane (TPU) and a second layer formed from a thermoplastic polymer-based coupling agent containing an ethylene-vinyl acetate (EVA) copolymer and a second polar co-monomer, wherein the barrier film has a total thickness of between 50 µm (2 mil) and 600 µm (24 mil), wherein the first layer has a thickness of between 20 µm (0.8 mil) and 400 µm (16 mil), and wherein the second layer has a thickness of between 20 µm (0.8 mil) and 200 µm (8 mil); and the aperture according to Clause 17.

Clause 20. A method of performing a medical procedure selected from the group consisting of a colostomy, a urostomy, and an ileostomy, the method comprising including the ostomy pouch according to Clause 19.

Clause 21. An ostomy pouch comprising a barrier film comprising a first layer formed from thermoplastic polyurethane (TPU) and a second layer formed from a thermoplastic polymer-based coupling agent containing an ethylene-vinyl acetate (EVA) copolymer and a second polar olefin copolymer, wherein the barrier film has a total thickness of between 50 µm (2 mil) and 600 µm (24 mil), wherein the first layer has a thickness of between 20 µm (0.8 mil) and 400 µm (16 mil), and wherein the second layer has a thickness of between 20 µm (0.8 mil) and 200 µm (8 mil) and the aperture according to Clause 17.

Clause 22. A method of constructing an ostomy pouch, the method comprising joining an olefinic film with a barrier film comprising a first layer formed from thermoplastic polyurethane (TPU) and a second layer formed from a thermoplastic polymer-based coupling agent containing an ethylene-vinyl acetate (EVA) copolymer and a second polar co-monomer, wherein the barrier film has a total thickness of between 50 µm (2 mil) and 600 µm (24 mil), wherein the first layer has a thickness of between 20 µm (0.8 mil) and 400 µm (16 mil), and wherein the second layer has a thickness of between 20 µm (0.8 mil) and 200 µm (8 mil) to form a multilayer film and forming a pouch comprising a first wall and a second wall joined together to define a closed compartment having an interior from the multilayer film.

What is claimed is:

1. A barrier film comprising
    a first layer formed from thermoplastic polyurethane (TPU); and
    a second layer formed from a thermoplastic polymer-based coupling agent containing an ethylene-vinyl acetate (EVA) copolymer and a second polar co-monomer,
    wherein the barrier film has a total thickness of between 50 µm (2 mil) and 600 µm (24 mil), the first layer has a thickness of between 20 µm (0.8 mil) and 400 µm (16 mil), and the second layer has a thickness of between 20 µm (0.8 mil) and 200 µm (8 mil), and wherein the ethylene-vinyl acetate (EVA) copolymer includes maleic anhydride in an amount of less than 5000 ppm.

2. The barrier film according to claim 1, wherein the ethylene-vinyl acetate (EVA) copolymer contains at least 15% vinyl acetate.

3. The barrier film according to claim 1, wherein the first layer has a Shore hardness, measured according to ASTM D 2240, of 75-95 A.

4. The barrier film according to claim 1, wherein the second layer comprises a blend of thermoplastic polyurethane (TPU) and ethylene-vinyl acetate (EVA) copolymer.

5. The barrier film according to claim 1, wherein the second layer comprises a blend of a thermoplastic polyurethane (TPU) and a modified ethylene-vinyl acetate (EVA) at a ratio between 0.3 mass-percent and 3.0 mass-percent.

6. The barrier film according to claim 1, wherein the second layer comprises a blend of a thermoplastic polyurethane (TPU) and a modified ethylene-vinyl acetate (EVA) at a ratio between 0.7 mass-percent and 1.5 mass-percent.

7. The barrier film according to claim 1, wherein the second polar co-monomer comprises one monomer selected from the group consisting of vinyl acetate, acrylic acid, acrylic acid esters, acrylic acid salts, methacrylic acid, methacrylic acid esters, and methacrylic acid salts.

8. The barrier film according to claim 1, wherein between 0% and 30% of an additive selected from the group consisting of anti-blocking agents, inorganic or organic spacers, slip or separation aids, pigments, fillers, and stabilizers, is added to the first layer.

9. The barrier film according to claim 1, wherein the film is produced in a co-extrusion process at a temperature of from 160° C. to 200° C.

10. The barrier film according to claim 9, wherein the film is produced in a blown film co-extrusion process at a temperature of from 160° C. to 200° C.

11. The barrier film according to claim 1, wherein at least one layer is subjected to a physical or chemical surface treatment.

12. The barrier film according to claim 1 further comprising an adhesive layer applied to the first layer.

13. The barrier film according to claim 12, wherein the adhesive comprises a polyurethane.

14. A laminated structure comprising the barrier film according to claim 1 joined to an olefin-based film.

15. The laminated structure according to claim 14, wherein the olefin is polyethylene.

16. The laminated structure according to claim 14, wherein the barrier film and the olefin-based are joined by a thermal joining method selected from the group consisting of thermo lamination and flame bonding.

17. An aperture comprising the laminated structure according to claim 14.

* * * * *